United States Patent
Gordley

(10) Patent No.: US 7,847,945 B2
(45) Date of Patent: Dec. 7, 2010

(54) MAKING AND USING DOPPLER SHIFTED MEASUREMENTS IN GAS FILTER CORRELATION RADIOMETRY

(75) Inventor: Larry L. Gordley, Grafton, VA (US)

(73) Assignee: G & A Technical Software, Inc., Newport News, VA (US)

( * ) Notice: Subject to any disclaimer, the term of this patent is extended or adjusted under 35 U.S.C. 154(b) by 90 days.

(21) Appl. No.: 12/387,731

(22) Filed: May 7, 2009

(65) Prior Publication Data

US 2010/0284011 A1    Nov. 11, 2010

(51) Int. Cl.
*G01N 21/00*    (2006.01)
(52) U.S. Cl. .................. 356/437; 356/438
(58) Field of Classification Search .......... 356/437, 356/438
See application file for complete search history.

(56) References Cited

U.S. PATENT DOCUMENTS 6,008,928 A * 12/1999 Sachse et al. ............. 359/246
2003/0112435 A1 * 6/2003 Sachse ..................... 356/364

* cited by examiner

*Primary Examiner*—Roy Punnoose
(74) *Attorney, Agent, or Firm*—Peter J. Van Bergen

(57) ABSTRACT

A method is provided for making and using measurements in gas filter correlation radiometry. A Gas Filter Correlation Radiometer (GFCR) instrument is moved in a region of space surrounding a heavenly body. An atmosphere of the heavenly body is viewed with the GFCR instrument along a first view direction with the atmosphere and the GFCR instrument experiencing a relative velocity of approximately zero. The atmosphere is also viewed with the GFCR instrument along at least one second view direction that is angularly separated from the first view direction such that atmospheric spectra associated with the second view direction appears Doppler shifted with respect to atmospheric spectra associated with the first view direction. A gas filter correlation radiometry application is performed using the measurement signals obtained from the different view directions.

24 Claims, 1 Drawing Sheet

MAKING AND USING DOPPLER SHIFTED MEASUREMENTS IN GAS FILTER CORRELATION RADIOMETRY

FIELD OF THE INVENTION

The invention relates generally to gas filter correlation radiometry, and more particularly to a method that makes and uses Doppler shifted measurements in a variety of gas filter correlation radiometry applications.

BACKGROUND OF THE INVENTION

Gas filter correlation radiometry is an optical remote sensing method used to produce highly sensitive measurements of target gases present in an atmospheric region. In general, gas filter correlation radiometer (GFCR) systems either use single-beam/single-detector or multi-beam/multi-detector measurement approaches to collect data from measurement views directed through an atmospheric region of interest. Both measurement systems include a gas cell containing a target gas of interest. Target gas presence in the observed atmosphere is indicated by examining signal changes induced when the target gas condition in the gas cell is changed. This change can be caused by modulating the gas pressure or effective cell length for single beam systems, or comparing signals from light that passed through different gas cells (or no cell) for multi-beam systems. Single-beam/single-detector measurement systems must be able to quickly change the effective cell condition by modulating the cell content or altering the light path to pass through various cells in order to properly evaluate an atmospheric region for a target gas. The multi-beam/multi-detector measurement systems split collected light and simultaneously pass the light through separate gas and vacuum cells. However, multi-beam/multi-detector systems must be stable and properly calibrated in order to mitigate error due to even minor drifts in detector response. Thus, both types of GFCR measurement systems have measurement sensitivities that can impact target gas detection capabilities.

SUMMARY OF THE INVENTION

Accordingly it is an object of the present invention to provide a method for making measurements that can be used in gas filter correlation radiometry.

Another object of the present invention is to provide a method of making GFCR measurements from a planetary orbit where the resulting measurements improve target gas detection capabilities.

Other objects and advantages of the present invention will become more obvious hereinafter in the specification and drawings.

In accordance with the present invention, a method is provided for making and using measurements in gas filter correlation radiometry. A Gas Filter Correlation Radiometer (GFCR) instrument capable of making a measurement viewing through a gas cell is required. The GFCR instrument is moved in a region of space surrounding a heavenly body along a velocity vector. An atmosphere of the heavenly body is viewed with the GFCR instrument along a first view direction with a small or near zero relative velocity between the atmosphere and the GFCR instrument. The GFCR instrument generates a first signal associated with the first view direction. The atmosphere is also viewed with the GFCR instrument along at least one second view direction that is angularly separated from the first view direction. The atmospheric spectra associated with the second view direction appears Doppler shifted with respect to atmospheric spectra associated with the first view direction. The GFCR instrument generates at least one second signal associated with and corresponding to the one or more second view directions. A gas filter correlation radiometry application is performed using the first signal and the one or more second signals.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
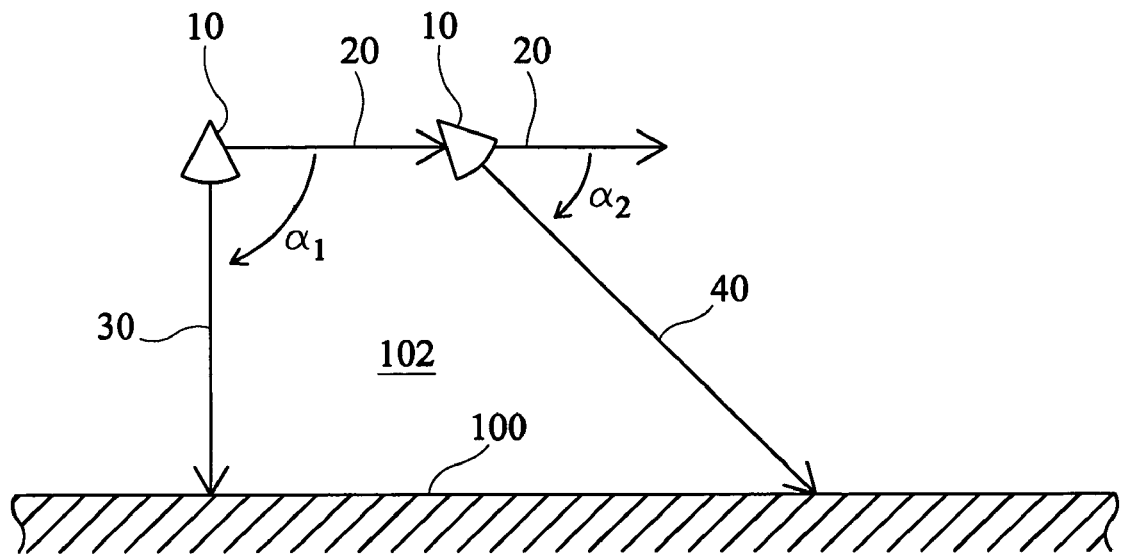
FIG. 1 is a schematic view of a gas filter correlation radiometer (GFCR) instrument traveling in a planetary orbit and taking measurements in accordance with an embodiment of the present invention.

Referring now to the drawings and more particularly to FIG. 1, a gas filter correlation radiometer (GFCR) instrument is shown and is referenced by numeral 10. GFCR instrument 10 is representative of either a single-beam/single-detector or a multi-beam/multi-detector GFCR measurement system, either of which can benefit from the measurement method of the present invention. By way of example, the present invention will be illustrated with a two-beam implementation. However, it is to be understood that the approach described herein applies equally as well to multi-beam implementations utilizing three or more beams.

For purposes of the present invention, GFCR instrument 10 is located in a space region above the surface 100 of a heavenly body that has an atmosphere 102 that can include a target gas of interest. For purpose of description, the heavenly body is the Earth, although the methods of the present invention will apply to any heavenly body with a surrounding atmosphere.

In accordance with the present invention, GFCR instrument 10 is moving in the space region along a velocity vector referenced by numeral 20. For many GFCR applications, GFCR instrument 10 will be traveling in a low orbit over surface 100 along velocity vector 20. Placement and movement of GFCR instrument 10 in space will typically be accomplished by mounting GFCR instrument 10 on an orbiting satellite platform (not shown) as would be understood in the art.

As is well known in the art of making GFCR measurements, GFCR instrument 10 is oriented to view a region of the atmosphere 102 along a view direction. For example, in the illustrated embodiment, a view direction 30 is approximately perpendicular to both velocity vector 20 and the surface 100 of the Earth. Solar light scattered from the surface 100 is measured by GFCR instrument 10 as it "views" the atmosphere 102 along view direction 30. As is known in the art, GFCR instrument 10 generates a signal indicative of the "view". If GFCR instrument 10 is a single-beam/single-detector system, the cell content through which light passes must be modulated. If GFCR is a two-beam/two-detector system, the light is split into two paths. A first path is directed through a gas cell containing target gas. A second path is directed either through a void/vacuum or a second gas cell with a fill condition that is different (e.g., typically void of any target gas) than the first cell.

In accordance with the present invention, the measurement made along view direction 30 is taken when the relative velocity between GFCR instrument 10 and the atmosphere 102 is zero or approximately zero. Solar light reflected by or scattered from the surface 100 is also measured by GFCR instrument 10 while viewing the atmosphere 102 along a second view direction 40 that is angularly displaced from view direction 30. That is, GFCR instrument 10 views atmosphere 102 along view direction 30 and generates a GFCR measurement signal indicative of atmospheric information in the view. After collecting the atmospheric data along view direction 30, GFCR instrument 10 is "pointed" to view atmosphere 102 along view direction 40 where another GFCR measurement signal is generated. The amount of time between such measurements and/or distance traveled by GFCR instrument 10 between such measurements are somewhat dependent on the gas filter correlation radiometry application that will use the measurements and are, therefore, not limitations of the present invention.

In general, if view direction 30 forms an angle of $\alpha_1$ with velocity vector 30, view direction 40 forms an angle of $\alpha_2$ with velocity vector 20 where $\alpha_1$ is different than $\alpha_2$. The amount of angular difference should be sufficient such that the atmospheric spectral features of the atmosphere 102 associated with view direction 40 appear Doppler shifted with respect to the atmospheric spectral features of the atmosphere 102 associated with view direction 30. The actual amount of angular difference will depend upon the gas filter correlation radiometry application using such measurements.

The present invention implements a measurement technique that includes observations (i.e., measurement views) of the atmosphere 102 (to include any target gas of interest) under conditions of Doppler shift. When view direction 40 views a region of the atmosphere 102 that is approaching GFCR instrument 10, the Doppler shift will cause the spectral features to stretch. Conversely, when view direction 40 views of a region of the atmosphere 102 that is moving away from GFCR instrument 10, the Doppler shift will cause the spectral features to contract. Shifting in either direction will spectrally separate the gas cell spectral features relative to the corresponding atmospheric spectral features thereby inducing a change in the GFCR signal that can provide information for a host of analytical applications.

The novel measurement strategy of the present invention provides a number of observational advantages when performing various gas filter correlation radiometry processes or applications. For example, some gas filter correlation radiometry applications will involve generating signal differences between Doppler shifted (e.g., along view direction 40) and unshifted (e.g., along view direction 30) observations. The signal differences can be highly correlated with the concentration of the target gas thereby yielding a signal (i.e., a difference signal) that is nearly a direct measure of the gas and relatively unaffected by signal offsets. This is especially effective for high altitude limb emission measurements where thermal emission is measured (instead of solar scatter) viewing toward the edge (limb) of the Earth in directions with different relative velocities between atmosphere and instrument. In addition, the effective high spectral resolution GFCR signals generated by Doppler shifted observations are mathematically equivalent to scanning the absorption or emission spectral features of the target gas. For a downward looking instrument, this provides altitude information as is well known in the art. For limb emission observations and solar occultation measurements, this can be used to calibrate the gas cell concentration because the signal as a function of Doppler velocity will be affected by the width of gas cell spectral features, which is a function of cell content. Further and as will be explained further below, shift observations that are predicted to induce near zero correlation between cell and atmospheric spectra can be used to determine the balance for a two-beam/two-detector GFCR instrument, which is critical to obtaining an accurate analysis of the two-beam difference signal.

Figure 2:
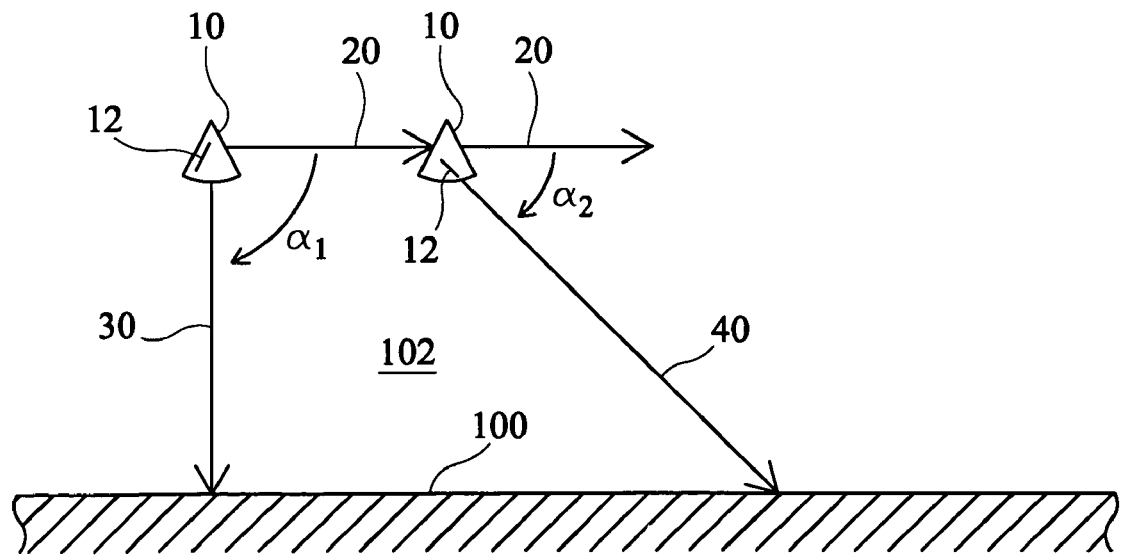
FIG. 2 is a schematic view of a GFCR instrument maintaining its orientation while traveling in a planetary orbit and taking measurements in accordance with another embodiment of the present invention.

The above-described measurement technique can be carried out in a variety of ways without departing from the scope of the present invention. The view(s) providing Doppler shifted measurements can be accomplished in a variety of ways, including tilting the entire instrument or rotating a pointing mirror that is part of the GFCR system. For example, making a measurement along view direction 40 could be accomplished by wholly re-orienting (e.g., tilting) GFCR instrument 10 relative to velocity vector 20 as illustrated in FIG. 1. This approach has the advantage of not disturbing the optical components and optical paths within GFCR instrument 10. However, the present invention could also be accomplished without changing the orientation of GFCR instrument 10 when making measurements along view directions 30 and 40. For example, FIG. 2 illustrates GFCR instrument 10 with internal steering optics 12 that can be used to control the instrument's view direction without changing the orientation of GFCR instrument 10. The particular choice of elements/systems comprising steering optics 12 is not a limitation of the present invention as the use and operation of such steering optics is well understood in the art. This approach has the advantage of not requiring activation of any re-orientation systems (e.g., spacecraft attitude control systems) in order to make Doppler shifted measurements.

While the approaches discussed above describe a single unshifted measurement and a single Doppler shifted measurement, the present invention is not so limited. The present invention could be expanded to various scanning measurement operations where the GFCR instrument collected measurement data along a variety of view directions. For example, multiple unshifted and shifted measurements could be obtained by periodically scanning back and forth between unshifted and Doppler shifted view directions (e.g., view directions having attributes like that of view directions 30 and 40). For other radiometry applications, a single unshifted measurement and a variety of Doppler shifted measurements (i.e., different Doppler shifts) could be collected. The particular measurement data and corresponding collection strategy would typically be predicated on the gas filter correlation radiometry application.

As mentioned above, the measurement approach described herein can be used in a variety of GFCR processes/applications. For example, the present method provides the data needed to calibrate a two-beam/two-detector GFCR instrument operating in a low-planetary orbit without requiring an on-board calibration system. More specifically, the present invention's measured data can be used to determine the balance of a two-beam GFCR instrument measuring scattered solar light without hardware or specific subsystems for this purpose. This is important because two-beam GFCR instruments are uniquely suited for using scattered sunlight to sense molecular concentrations in the planetary boundary layer (i.e., near the surface). However, the relative system response to the two beams (i.e., the "balance" as it is also known) must be determined very accurately. The measurement approach of the present invention facilitates the solving of this problem.

Typical methods of calibrating the balance of a two-beam GFCR instrument measuring scattered solar light involve creating an observation in which the light source is known and there is no intervening gas between the instrument and the source of light. In that way, the response (or balance) can be determined. Historical approaches involve creating a light source either internally or externally in an attempt to spectrally mimic the observation light source. Traditionally, this is done with a "diffuser plate" that scatters sunlight as it is periodically placed in front of the instrument aperture. Another method dynamically changes the instrument's optical configuration to bring an internal source into view. These methods require additional instrument complexity and often introduce spectral uncertainty and potential error due to long-term change/drift in calibrated response error.

When atmospheric spectra is Doppler shifted as is the case using the measurement method of the present invention, it can be shown that there is a degree of shift where the ratio of the two signals (e.g., the gas path and vacuum path signals from a two-beam GFCR instrument) is nearly identical to their ratio when observing an unattenuated source (i.e., no intervening atmosphere). This ratio determines the instrument's balance. Note that it is not always necessary to observe the same air for both shifted and unshifted observations.

By simply "pointing the GFCR instrument" (e.g., overall instrument movement or via internal optics adjustments) to look somewhat forward or backward along the instrument's velocity vector, a Doppler shifted atmospheric spectra can be observed and then used to determine the balance. This approach has the added feature that the source function of the primary science observations is also the calibrating source function, which will not degrade over time. It also has the advantage of using exactly the same optical configuration for both science and calibration observations when the instrument platform provides the pointing.

A mathematical analysis using Doppler shifted data to determine balance of a two-beam GFCR instrument will now be described. A typical two-beam GFCR instrument divides an incoming beam into two beams ($I_g$ and $I_v$) and passes one beam ($I_g$) through a gas cell containing the type of gas to be detected, and then on to a detector. The other beam ($I_v$) is passed through a vacuum cell, and then on to another detector. The intensities of the two beams, $I_g$ and $I_v$, are measured. Specifically, the measurements are:

$$M_v = C_v I_v \quad (1)$$

$$M_g = C_g I_g \quad (2)$$

where $I_g = \int S(v) f(v) \tau_g(v) \tau_a(v) dv$ $I_v = \int S(v) f(v) \tau_a(v) dv$ S=a source function (e.g., the sun if the instrument is above the Earth)

f=the broadband spectral filter $\tau_g$=transmission of gas in cell $\tau_a$=transmission of observed atmosphere v=wavenumber S, f and $\tau$ are functions of wavenumber $C_g$ and $C_v$ are unknown response constants The integration is over the non-zero extent of the filter function f. For the beam $I_v$ that does not pass through the cell, $\tau_g$ is set to 1.0. The ratio $I_g/I_v$ can be used to infer the extinction due to the target gas in the observed path, which is the basis of the two-beam GFCR technique.

To determine $I_g/I_v$, the balance $C_g/C_v$ must be known where, from equations 1 and 2, $$I_g/I_v = (M_g/M_v)^*(C_v/C_g) \quad (3)$$

The traditional solution to finding the balance is to create a measurement with an onboard source, often a solar diffuser plate, that produces an observation where $I_g^c/I_v^c$ is known and, ideally, produces a measurement ratio identical to an observation with no atmospheric attenuation. Based on this assumption, the balance relationship can be written as $$(C_v/C_g) = (M_v^c/M_g^c)(I_g^c/I_v^c) \quad (4)$$

where the superscript "c" indicates the observation of a calibration source. Substituting equation (4) into equation (3) yields $$I_g/I_v = (M_g/M_v)(M_v^c/M_g^c)(I_g^c/I_v^c) \quad (5)$$

It has been found that standard observations of the atmosphere under conditions of a specific predictable Doppler shift, D, produce a signal ratio nearly identical to the ideal calibration ratio. That is, $$M_g^D/M_v^D \cong M_g^c/M_v^c \quad (6)$$

This is true because under conditions of increasing Doppler shift (i.e., either negative or positive shift), the atmospheric spectra shifts causing the target gas spectra to shift away from the gas cell absorption features thereby decreasing the ratio of $I_g/I_v$. In fact for most atmospheric conditions $$I_g^{DO}/I_v^{DO} > I_g^c/I_v^c > I_g^{DM}/I_v^{DM}$$

where the superscript "DO" indicates zero shift and the superscript "DM" indicates maximum observable shift. Therefore, there is a shift (designated by the superscript "D") that is accurately predicted by model, and lies between DO and DM that will produce the calibration ratio.

Calculations show that with careful selection of shift and bandpass, $(M_g^D/M_v^D - M_g^c/M_v^c) < (1 \times 10^{-5})$. The residual difference can be modeled (predicted) to provide additional accuracy. The Doppler shift is well known through orbit and pointing knowledge, and the sensitivity to cell condition can be very low.

From equations (5) and (6), $$I_g/I_v = (M_g/M_v)(M_v^D/M_g^D)(I_g^c/I_v^c)$$

The result is that the ratio $I_g/I_v$ can be determined from (i) Doppler shifted and unshifted measurements, and (ii) the ratio $I_g^c/I_v^c$, which is a function of the known quantities of cell content ($\tau_g$) and the broad spectral bandpass (f).

The advantages of the present invention are numerous. The measurement approach can be readily implemented with existing GFCR instruments. Unshifted and Doppler shifted measurements are made with the same optical configuration so that science and calibration measurements are made with identical hardware configurations. The measurement approach can produce data that will yield improved results in a variety of GFCR processes and applications.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A method of making and using measurements for gas filter correlation radiometry, comprising the steps of:
    providing a Gas Filter Correlation Radiometer (GFCR) instrument capable of making a measurement viewing through a gas cell;
    moving the GFCR instrument in a region of space surrounding a heavenly body along a velocity vector;
    viewing an atmosphere of the heavenly body with the GFCR instrument along a first view direction wherein the atmosphere and the GFCR instrument experience a relative velocity of approximately zero along said first view direction, wherein the GFCR instrument generates a first signal associated with said first view direction;
    viewing the atmosphere with the GFCR instrument along at least one second view direction that is angularly separated from said first view direction wherein atmospheric spectra associated with said second view direction appears Doppler shifted with respect to atmospheric spectra associated with said first view direction, wherein the GFCR instrument generates at least one second signal associated with and corresponding to said at least one second view direction; and
    performing a gas filter correlation radiometry application using said first signal and said at least one second signal.

2. A method according to claim 1, further comprising the step of periodically repeating said steps of viewing.

3. A method according to claim 1, wherein said step of viewing the atmosphere with the GFCR instrument along said at least one second view direction comprises the step of viewing the atmosphere with the GFCR instrument along a plurality of second view directions.

4. A method according to claim 3, wherein atmospheric spectra associated with each of said plurality of second view directions is uniquely Doppler shifted.

5. A method according to claim 1, wherein said step of moving comprises the step of orbiting the GFCR instrument around the heavenly body.

6. A method according to claim 1, wherein said step of moving includes the step of positioning the GFCR instrument in an orbit above the heavenly body.

7. A method according to claim 1, wherein the heavenly body is the Earth.

8. A method according to claim 1, wherein said step of viewing along said second view direction includes the step of re-orienting the GFCR instrument with respect to the velocity vector.

9. A method according to claim 1, wherein said steps of viewing include the step of maintaining orientation of the GFCR instrument with respect to the velocity vector.

10. A method according to claim 1, wherein the GFCR instrument is a two-beam GFCR instrument capable of making a first measurement viewing through the gas cell and a second measurement viewing through a vacuum cell, and wherein said step of performing comprises the step of determining a balance of the two-beam GFCR instrument.

11. A method according to claim 1, wherein said step of performing includes the step of generating a difference signal between said first signal and said at least one second signal.

12. A method according to claim 11, wherein the GFCR instrument is a two-beam GFCR instrument capable of making a first measurement viewing through the gas cell and a second measurement viewing through a vacuum cell, and wherein said step of performing comprises the step of determining a balance of the two-beam GFCR instrument.

13. A method according to claim 1, wherein said first view direction is approximately perpendicular to the velocity vector.

14. A method according to claim 1, wherein said first view direction is approximately perpendicular to a surface of the heavenly body.

15. A method of making and using measurements in gas filter correlation radiometry, comprising the steps of:
    providing a Gas Filter Correlation Radiometer (GFCR) instrument capable of making a measurement viewing through a gas cell;
    positioning the GFCR instrument in a region of space above a heavenly body;
    orbiting the GFCR instrument around the heavenly body along a velocity vector;
    viewing an atmosphere of the heavenly body with the GFCR instrument along a first view direction wherein the atmosphere and the GFCR instrument experience a relative velocity of approximately zero along said first view direction, wherein the GFCR instrument generates a first signal associated with said first view direction;
    viewing the atmosphere with the GFCR instrument along at least one second view direction that is angularly separated from said first view direction wherein atmospheric spectra associated with said second view direction appears Doppler shifted with respect to atmospheric spectra associated with said first view direction, wherein the GFCR instrument generates at least one second signal associated with and corresponding to said at least one second view direction; and
    performing a gas filter correlation radiometry application using said first signal and said at least one second signal.

16. A method according to claim 15, further comprising the step of periodically repeating said steps of viewing.

17. A method according to claim 15, wherein said step of viewing the atmosphere with the GFCR instrument along said at least one second view direction comprises the step of viewing the atmosphere with the GFCR instrument along a plurality of second view directions.

18. A method according to claim 17, wherein atmospheric spectra associated with each of said plurality of second view directions is uniquely Doppler shifted.

19. A method according to claim 15, wherein the heavenly body is the Earth.

20. A method according to claim 15, wherein said step of viewing along said second view direction includes the step of re-orienting the GFCR instrument with respect to the velocity vector.

21. A method according to claim 15, wherein said steps of viewing include the step of maintaining orientation of the GFCR instrument with respect to the velocity vector.

22. A method according to claim 15, wherein said step of performing includes the step of generating a difference signal between said first signal and said at least one second signal.

23. A method according to claim 15, wherein said first view direction is approximately perpendicular to the velocity vector.

24. A method according to claim 15, wherein said first view direction is approximately perpendicular to a surface of the heavenly body.

* * * * *